United States Patent [19]

Tillmanns

[11] Patent Number: 5,604,532
[45] Date of Patent: Feb. 18, 1997

[54] APPARATUS AND METHOD FOR INSITU INSPECTION OF PRESSURIZED VESSELS

[76] Inventor: Josef Tillmanns, 2316 Main St., Patterson, La. 70392

[21] Appl. No.: 548,260

[22] Filed: Oct. 25, 1995

Related U.S. Application Data

[63] Continuation of Ser. No. 254,579, Jun. 6, 1994, abandoned.

[51] Int. Cl.$^6$ .................................................. H04N 7/18
[52] U.S. Cl. ............................ 348/84; 348/85; 348/83
[58] Field of Search .................................. 348/81, 82, 83, 348/84, 85

[56] References Cited

U.S. PATENT DOCUMENTS

| | | | |
|---|---|---|---|
| 3,021,386 | 2/1962 | Clark | 178/6 |
| 3,075,113 | 1/1963 | Soar | 313/17 |
| 3,780,571 | 12/1973 | Wiesener | 73/67.85 |
| 4,302,772 | 11/1991 | Gillot | 348/84 |
| 4,725,883 | 2/1988 | Clark, Jr. et al. | 348/84 |
| 4,729,423 | 3/1988 | Martin | 348/82 |
| 4,855,820 | 8/1988 | Barbour | 348/82 |
| 4,915,013 | 4/1990 | Harth et al. | 376/248 |
| 4,965,601 | 10/1990 | Canty | 354/63 |
| 4,977,418 | 12/1990 | Canty | 354/63 |
| 4,998,282 | 3/1991 | Shishido et al. | 381/77 |
| 5,068,720 | 11/1991 | Herlitz | 358/100 |
| 5,084,764 | 1/1992 | Day | 348/84 |

*Primary Examiner*—Thai Q. Tran
*Assistant Examiner*—Anand Rao
*Attorney, Agent, or Firm*—Harrison & Egbert

[57] ABSTRACT

An apparatus and method for inspecting the internal surfaces of a pressurized vessel, without disturbing the pressurized environment within the vessel. A specially configured apparatus is inserted through an open bore valve and emulates a chamber having like pressure with the pressurized vessel. A camera housing containing a CCTV camera is inserted through an open bore valve to enable in situ inspection the interior of a pressurized vessel without having to bleed off this pressure. The camera is inserted into the interior from a sealed connector pipe. A camera housing assembly gains entry to a predetermined depth in the vessel by a sealed reach pipe which rotates freely under pressure. A control pipe located axially inside the reach pipe controls camera tilt.

17 Claims, 3 Drawing Sheets

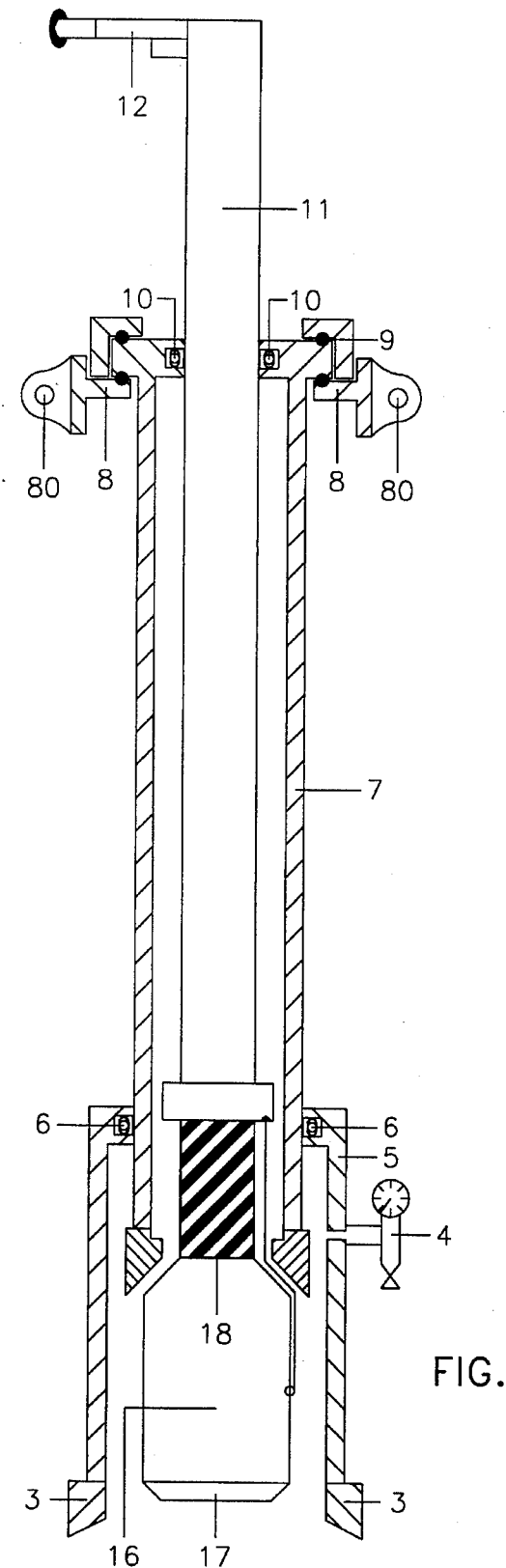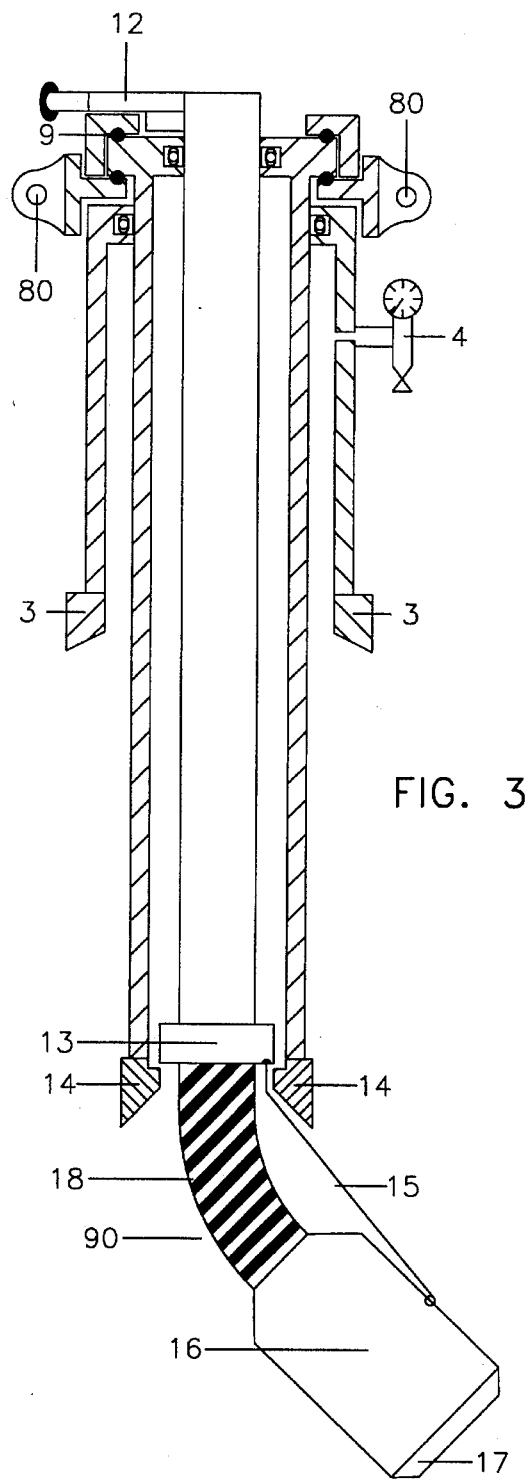
FIG. 2
FIG. 3

APPARATUS AND METHOD FOR INSITU INSPECTION OF PRESSURIZED VESSELS

This is a continuation of application Ser. No. 08/254,579, filed on Jun. 06, 1994, now abandoned.

BACKGROUND OF THE INVENTION

This invention relates to inspection methods and apparatus, and more particularly relates to methods and means for inspecting pressurized vessels in situ.

It is well known in the prior art that inspecting pressurized vessels is time-consuming and labor-intensive. It is also well known that such inspection operations are hazardous not only to workers but also to the environment.

It is also well known in the prior art that certain pressure vessels such as railway tankcars must be inspected to comply with federal government regulations intended to prevent contamination and perhaps invasion of the environment by industrial waste and contaminants. Thus, such inspections are unavoidable and must be performed on a regular basis.

Personnel engaged in inspecting pressurized vessels typically are required to wear protective clothing, chemical-resistant gloves and use respiratory devices. Personnel frequently are required to actually enter vessels to ascertain whether there is any contamination and the like therein. Procedures generally followed in the art are thus inherently hazardous and are, of course, unpopular among workers. There have been several attempts in the art to improve inspection methodology by providing apparatus which addresses some of these inherent disadvantages and limitations.

For example, in U.S. Pat. No. 5,068,720, Herlitz et at. teach a video inspection system for hazardous environments which comprises a sealed, pressurized housing with a lens affixed across a view window, and a camera mounted within the housing, for recording visual images. Fiber optics may be use to transmit signals from the camera to a recording device. The Herlitz device appears to fail to provide sufficient panning and tilting maneuverability to view all of the interior surfaces of a pressurized vessel without disturbing the pressurized environment inside the vessel and by being inserted into the vessel through an existing port of entry and the like.

As another example, Canty, in U.S. Pat. Nos. 4,965,601 and 4,977,418, teaches apparatus for viewing inside pressure vessels through an aperture in its side. More particularly, U.S. Pat. No. 4,977,418 discloses a hermetically-sealed, explosion-proof aluminum housing containing a charge coupled device (CCD) camera with a fused lens at its front end. This camera is spring-mounted on slide beatings for focusing, which is achieved by externally adjusting a screw or a servo motor located rearward in the housing. Similarly, U.S. Pat. No. 4,965,601 discloses a viewing unit comprising a CCD or CCTV camera having a fused lens attached immediately in front of a fixed lens. The fixed lens is surrounded by a shoulder with a threaded periphery for attaching it to a corresponding aperture in the vessel. Focusing is achieved by turning the camera relative to a threaded portion of the fixed lens housing. An apparent disadvantage of this embodiment is that them is a tendency to unscrew the fused attachment from the connection with the vessel.

In U.S. Pat. No. 4,302,772, Gillot teaches a device for televisual inspection of a closed cylindrical water-containing pressurizer vessel, wherein the device enters the vessel through an aperture. The Gillot apparatus comprises a television camera suspended from a flexible tube and floodlights, with the flexible tube being oriented over its path into the interior of the vessel by a rigid tubular guide. The tube is caused to rotate about its axis preventing the camera from experiencing axial movement, thereby providing improved televisual data with the vacuum intake manifold.

Similarly, in U.S. Pat. No. 3,780,571, Wiesener discloses an apparatus which is inserted within a nuclear reactor pressure vessel for diagnosing whether routine maintenance is required. The apparatus is designed to operate under typical reactor cooling water without pressurized air. Clark discloses, in U.S. Pat. No. 3,021,386, an apparatus using CCTV to view interior boiler walls and project the images to a remote location without damaging the camera. An elongated lens extending through an aperture provides for view adjustments.

While, as hereinbefore exemplified, practitioners in the art have attempted to improve the means and methods for inspecting pressurized vessels, there has not been an improvement in the art which affords a reliable and convenient procedure for performing such inspection without impacting the pressurized contents of the vessel. Accordingly, these limitations and disadvantages of the prior art are overcome with the present invention, and improved means and techniques are provided which are useful for inspecting pressurized vessels in situ.

SUMMARY OF THE INVENTION

The present invention provides an improved apparatus and method for inspecting the internal surfaces of a pressurized vessel, without disturbing the pressurized environment within the vessel. In accordance with the present invention, a specially configured apparatus is inserted through an open bore valve and the like, and effectively creates a telescopic chamber having like pressure with the pressurized vessel. More particularly, a camera housing containing a color closed circuit television ("CCTV") camera is inserted through a quarter turn or open bore valve to enable in situ inspection of the interior of a pressurized vessel without having to bleed off this pressure, thereby saving time and avoiding safety hazards to workers and avoiding contaminating the vessel and the environment.

The CCTV camera is inserted into the interior from a sealed connector pipe through an open bore valve typically located on top of the vessel. A pressure proof corrosion resistant camera housing assembly gains entry to a predetermined depth in the vessel by a sealed reach pipe which rotates freely under pressure, affording a 360° degree panning action of the camera. Another pipe having a smaller diameter than the reach pipe and referred to as a tilt control pipe, is located axially inside the reach pipe. The control pipe is sealed on its circumference to the inside annulus of the reach pipe. As will be hereinafter described in detail, the control pipe provides tilt action of the camera housing which, in turn, controls the angle with which the camera views the interior surfaces of the pressurized vessel.

The interior of the control pipe is open to the camera housing which is connected with a flex pipe, providing a conduit for accessing the interior of the camera housing to inertly remove any oxygen therein by inserting 100% nitrogen gas under pressure from the surface.

Accordingly, the present invention improves upon visual inspections which heretofore required bleeding off hazardous gasses and the like, which constitute a threat to the environment and to personnel.

Accordingly, in accordance with the present invention, methods and means are provided to enable a pressurized vessel to be inspected in situ without disturbing either the pressurized conditions therein or without invading the ambient.

It is an object of the present invention to provide a method and means for conveniently and reliably inspecting the interior surfaces of pressurized vessels in situ.

It is also an object of the present invention to provide a method and apparatus for inspecting the interior surfaces of pressurized vessels without necessitating significant downtime of the vessels.

It is a further object of the present invention to provide an apparatus and method for inspecting the interior surfaces of pressurized vessels without filtering gasses contained therein.

It is another object of the present invention to provide an apparatus and method for inspecting the interior surfaces of pressurized vessels without requiring workers to wear protective clothing and to use cumbersome breathing apparatus and the like.

It is still another object of the present invention to provide an apparatus and method for inspecting the interior surfaces of pressurized vessels consuming only minimal worker-time.

It is a feature and advantage of the present invention that inspection of pressurized vessels may be performed in situ by inserting an embodiment thereof through an open bore valve, with a convenience and reliability heretofore unknown in the prior art. It is accordingly an object of the present invention to provide an improved method and means for inspecting pressurized vessels with full panoply of pan and tilt maneuverability.

It is a specific object of the present invention to provide, an apparatus for in situ inspection of interior surfaces of a pressurized vessel having valve means for regulating said pressure therein, said apparatus comprising: a connector pipe means releasably and sealably attached at one end to said valve means and configured at its other opposite end to axially and sealably receive a concentric reach pipe means; said reach pipe means configured at one end disposed within said connector pipe means to be abuttably received by retainer means and configured at its other opposite end disposed outside of said connector pipe to slidably and sealably receive a control pipe means; said control pipe means disposed axially and sealably within said reach pipe means, and having a camera housing assembly manipulatively attached at an end contained proximal to said retainer means and having an insertion means fixedly attached at its opposite remote end; a first umbilical cable means axially contained within said control pipe means and interconnecting with said camera housing assembly and a power supply means, and further interconnecting said camera housing assembly with external viewing and recording means; and a second umbilical cable means axially contained within said control pipe means and interconnecting said camera housing assembly and a lighting means.

These and other objects and features of the present invention will become apparent from the following detailed description, wherein reference is made to the figures in the accompanying drawings.

IN THE DRAWINGS

FIG. 2 depicts a front cross sectional view of the apparatus depicted in FIG. 1.

FIG. 3 depicts another front cross sectional view of the apparatus depicted in FIG. 2.

DETAILED DESCRIPTION

Figure 1:
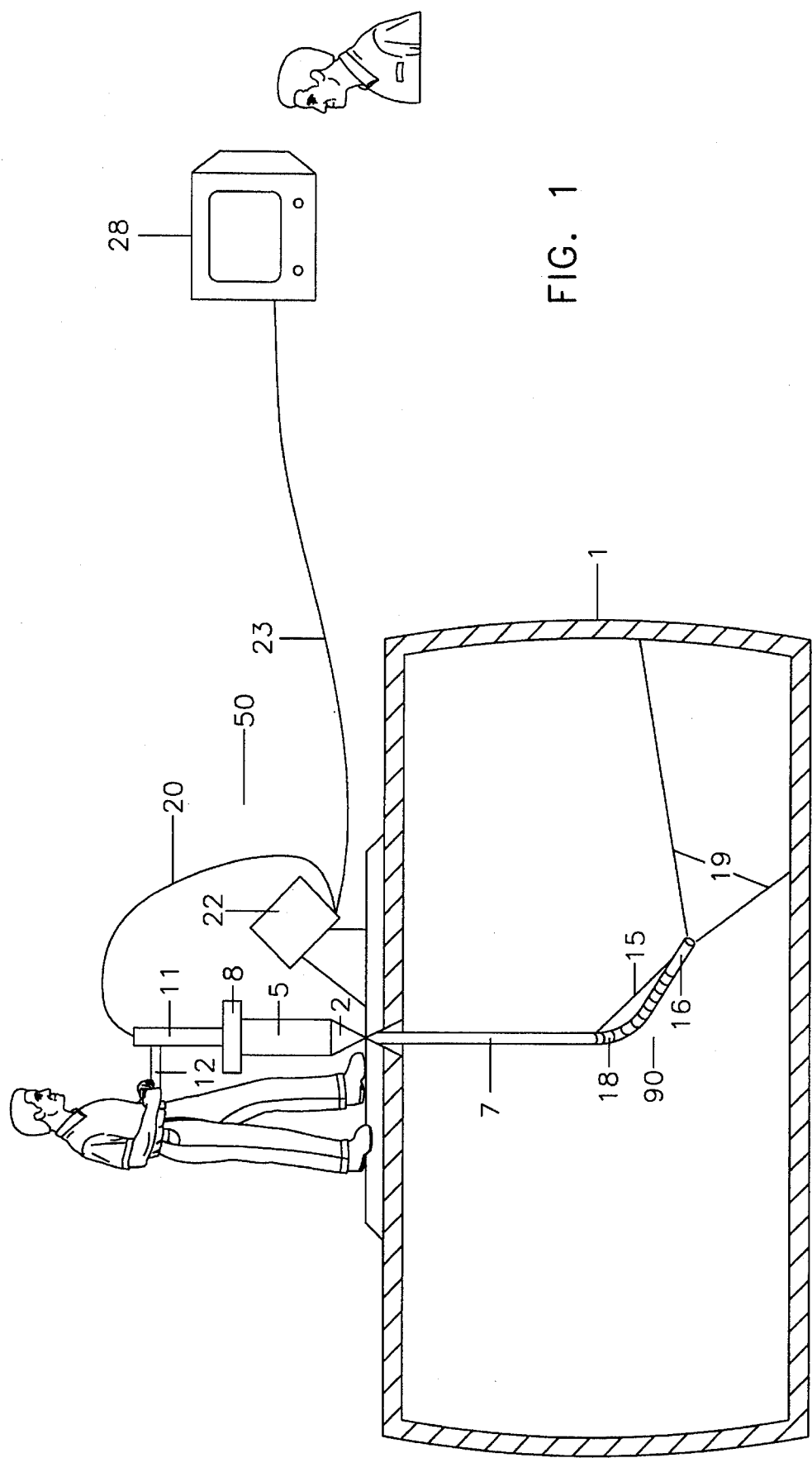
FIG. 1 depicts a frontal perspective view of an apparatus embodying the present invention.

FIG. 1 depicts a frontal perspective view of preferred embodiment of apparatus 50 for in situ inspection of pressurized vessels in accordance with the present invention. More particularly, there is shown high pressure vessel 1 with conventional bore valve and the like 2 which is interconnected with connector pipe 5. According to the teachings of the present invention, when valve 2 is open, as will hereinafter be described in detail, connector pipe 5 is attached thereto and reach pipe 7 is then inserted therethrough to enter the vessel, by a worker applying pressure to insertion or handle means 12. Thus, as reach pipe 7 is slowly and gradually introduced into vessel 1, control pipe 11 disposed axially therein, is caused to be correspondingly inserted thereinto. Simultaneously, flex pipe 18 is caused to tilt with consequent articulation of camera housing 16.

Still referring to FIG. 1, there is also shown rotating securing ring 8 which helps provide a sealable relationship between reach pipe 7 and control pipe 11. Reach pipe 7, in addition to concentrically enclosing control pipe 11, provides an enclosure for an umbilical cable for a closed circuit television ("CCTV") camera and for preferably an optic fiber cable, both being contained within a conduit represented as numeral 20 for simplicity. Tie-back strap 15 promotes the articulation of preferably pressure-proof camera housing 16 as will be hereinafter described. As a camera (not shown) contained within camera housing 16 views interior surfaces of vessel 1 through angle 19, enjoying the benefit of light communicated through the optical fiber cable, from its end proximal to television 22 to the distal end of optic fiber cable, corresponding signals are transmitted back to television 22 along the umbilical cable. Through using suitably powered cables 23 these signals may even be transmitted from locations proximal to the power supply at television 22 to remote locations, e.g. a location represented as numeral 28.

Referring now to FIGS. 2 and 3, the teachings of the present invention may be readily described in detail. Conventional camlock 3 provides a quick and reliable means for sealably attaching connector pipe 5 to open bore valve 2 (FIG. 1 ). Combination bleed-off valve and pressure gauge 4 provides means for regulating the pressure within an apparatus constructed according to the present invention, wherein the pressure therein is substantially the same as the pressure in vessel 1. Conventional reciprocating seal 6 affords prerequisite integrity for the joinder of reach pipe 7 and connector pipe 5. Circumferentially positioned along rotating locking ring 8 are a plurality of loops or eyes 80 to which may be releasably attached weights to counterbalance the pressure within vessel 1. More particularly, in applications in which the pressure within vessel 1 is about 30 psi, the weight of the instant apparatus including a suitable camera contained within camera housing 16 is sufficient to sustain the position thereof during inspection operations. If, however, internal pressures are significantly higher than 30 psi, then counter weights will be needed for stability purposes. Accordingly, appropriate counterbalancing weights may be attached to plurality of eyes 80. It has been found to be advantageous to configure securing ring 8 within a thrust bearing housing 9, to accommodate impact due to pressure effects and the like.

Still referring to FIGS. 2 and 3, there is seen reciprocating seal 6 disposed at the interface between reach pipe 7 and connecting pipe 5. Control pipe 11 is axially contained within reach pipe 7 and is fixedly attached to camera housing assembly 90. In particular, camera housing assembly 90 comprises flex pipe 18 fixedly attached to camera housing 16, which in turn contains a suitable camera (not shown) with lens means adjacent viewing port 17. Retainer 14 is fixedly attached to reach pipe 7 and is configured to abuttably receive slide ring 13 interconnecting control pipe 11 and flex pipe 18. At the opposite end of control pipe 11 is handle means 12 which is used to push control pipe into vessel 1, thereby introducing camera housing 16 further into the interior region of vessel 1 to be inspected. As will be hereinafter described, as pressure upon handle 12 and the like is continuously applied, after slide ring 13 is slidably received by retaining means 14, strap 15 is tightened, thereby causing flex pipe 18 to bend. Thus, by suitably pushing handle 12, viewing angle 19 may be varied as camera housing assembly 90 is caused to tilt as a result of this telescopic insertion of control pipe 11 within reach pipe 7. A rotation of reach pipe 7 causes camera housing assembly 90, including control pipe 11, to rotate view virtually all of the interior surfaces of vessel 1. Of course, other insertion means may be used, other than handle 12, to accomplish the necessary gradual telescopic insertion of reach pipe 7 and therein contained control pipe 11 into vessel 1. This action, as should be clear to those skilled in the art, in turn, causes camera housing 16 to tilt, thereby varying viewing angle 19 of port 17.

Figure 4:
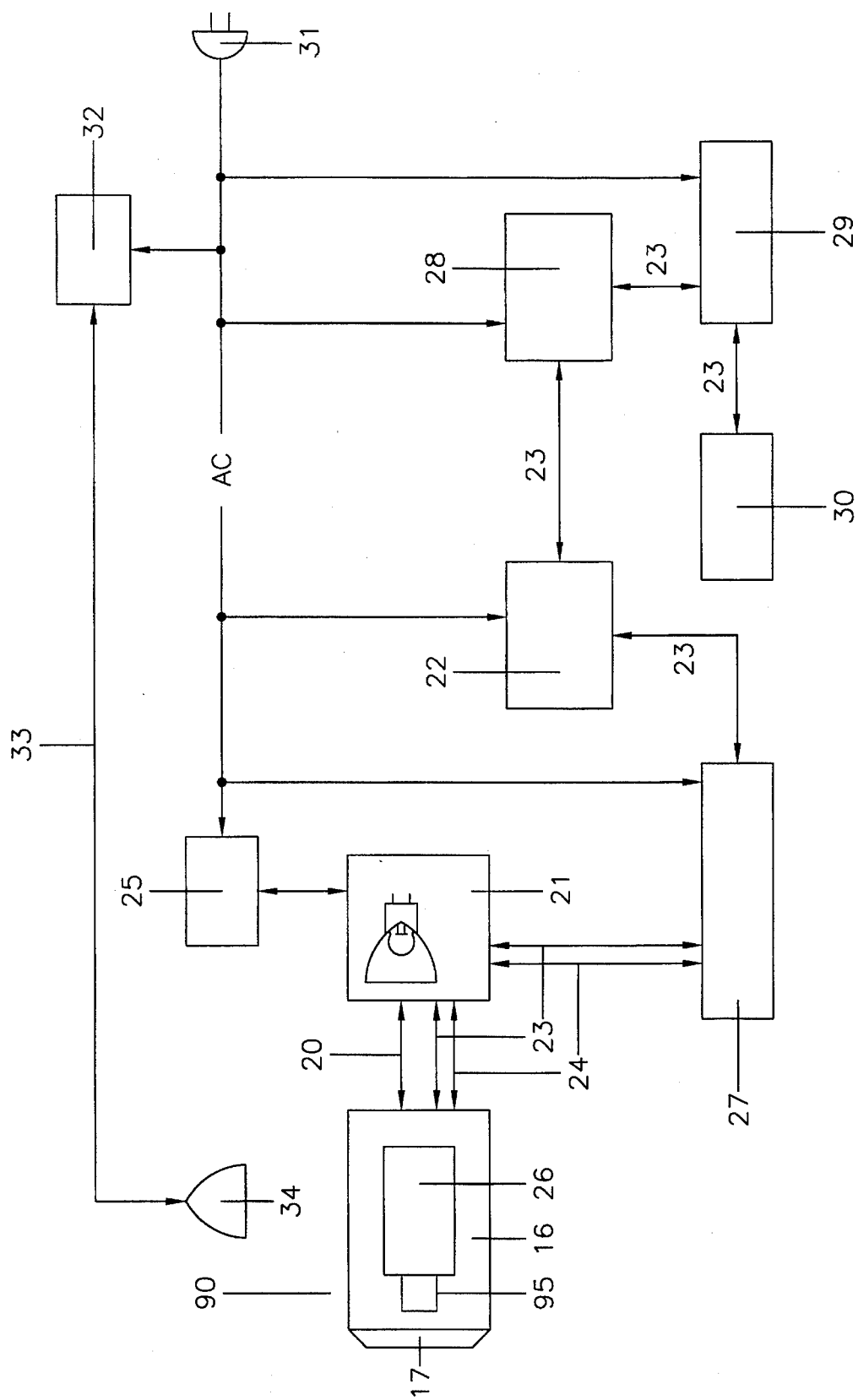
FIG. 4 depicts a simplified schematic diagram of the apparatus embodying the present invention.

Referring now to FIG. 4, there is shown a simplified flow chart schematically representing the components comprising the present invention. Camera housing assembly 90 comprises camera housing 16 having viewing port 17 for camera housing 16 contains CCTV camera 26 and lenses 95. As should be apparent to those skilled in the art, optic fiber cable contained within conduit 20 provides suitable illumination of interior surfaces through port 17. Video signals 23 from camera 26 are transmitted along umbilical cable 24 also contained within conduit 20. Also shown in power supply 27 with variable transformer 25 for light source 21 through optic fiber means contained within conduit 20 to port 17 of camera 26. Camera 26 receives power from power supply 27 across umbilical cable 24. Electrical power supply 31 provides power to the present invention which may include video cassette recorder and the like 29, remote TV monitor 28 and video frame storage and printing equipment with an integrated time/date generator 30. Two-way radio 32 with umbilical cable 33 may also be used to afford communication between a local operator and personnel at remote locations. In addition, as is well known in the art, two-way speaker or headset and microphone means 34 may be used.

Now referring collectively to FIGS. 1–4, the inspection procedure advantageously afforded by embodiments of the present invention will be described on a detailed stepwise basis. The particular illustration described hereinafter will be for inspection of a vessel having a conventional straight quarter-turn ball valve.

| Step | Description |
|---|---|
| 1. | Attach conventional male camlock to straight bore valve 2. |
| 2. | Stab female camlock 3 at distal end of connector pipe 5, and lock to male camlock. |
| 3. | Turn on power to camera 27, monitor 22 and light source 25, after connection is made and confirmed. |

| Step | Description |
|---|---|
| 4. | Close bleed-off valve on pressure regulating means 4 |
| 5. | Open valve 2, read pressure on gauge attached to pressure regulating means 4, add appropriate weights to plurality of eye hooks 80, when vessel internal pressure exceeds 30 PSI. |
| 6. | Push camera housing assembly 90 with reach pipe 7 through fully open valve 2 and insert into vessel 1 until rotating locking ring 8 establishes contact with the top of connector pipe 5 and locks into place. In the preferred embodiment, this locking mechanism is accomplished using two pins disposed 180° relative to each other. |
| 7. | Push control pipe 11 downward via handle 12 until tilt slide ring 13 reaches slide ring retainer 14 |
| 8. | To activate camera tilt operation, (FIG. 3) slowly continue pushing control pipe 11 downward to tighten tieback strap 15 as slide ring 13 is retained inside of reach pipe 7 due to slide ring retainer 14. To activate flex pipe 18, continue pushing control pipe 11 downward until handle 12 locks into reach pipe 7 thrust bearing assembly 9. |
| 9. | To activate panning operation, rotate reach pipe 7 at rotating locking ring 8 to the appropriate position for viewing. |
| 10. | The light intensity delivered to the distal end of the optic fiber 20 is varied at lamp 21 with variable transformer 25, which are located at the opposite end of optic fiber 20, to obtain maximum viewing illumination. |
| 11. | Once inspection is completed, to withdraw an embodiment of the present invention from vessel 1, pull up control pipe 11 via handle 12 to a predetermined stop, thereby bringing the camera housing 16 back to the relative position depicted in FIG. 2. |
| 12. | Release rotating locking ring 8 from connector pipe 5 and slowly withdraw reach pipe 7 and camera housing assembly 90 from pressurized vessel 1 through open ball valve 2 to a predetermined stop. |
| 13. | Close ball valve 2 and slowly release pressure from connector pipe 5 and the annulus of reach pipe 7, by opening the bleed-off valve contained on pressure regulating assembly 4. |
| 14. | Release female camlock 3 and remove the embodiment of the present invention from valve 2 and associated male cam lock. |

5. Open valve 2, read pressure on gauge attached to pressure regulating means 4, add appropriate weights to plurality of eye hooks 80, when vessel internal pressure exceeds 30 PSI.

6. Push camera housing assembly 90 with reach pipe 7 through fully open valve 2 and insert into vessel 1 until rotating locking ring 8 establishes contact with the top of connector pipe 5 and locks into place. In the preferred embodiment, this locking mechanism is accomplished using two pins disposed 180° relative to each other.

7. Push control pipe 11 downward via handle 12 until tilt slide ring 13 reaches slide ring retainer 14

8. To activate camera flit operation, (FIG. 3) slowly continue pushing control pipe 11 downward to tighten tieback strap 15 as slide ring 13 is retained inside of reach pipe 7 due to slide ring retainer 14. To activate flex pipe 18, continue pushing control pipe 11 downward until handle 12 locks into reach pipe 7 thrust bearing assembly 9.

9. To activate panning operation, rotate reach pipe 7 at rotating locking ring 8 to the appropriate position for viewing.

10. The light intensity delivered to the distal end of the optic fiber 20 is varied at lamp 21 with variable transformer 25, which are located at the opposite end of optic fiber 20, to obtain maximum viewing illumination.

11. Once inspection is completed, to withdraw an embodiment of the present invention from vessel 1, pull up control pipe 11 via handle 12 to a predetermined stop, thereby bringing the camera housing 16 back to the relative position depicted in FIG. 2.

12. Release rotating locking ring 8 from connector pipe 5 and slowly withdraw reach pipe 7 and camera housing assembly 90 from pressurized vessel 1 through open ball valve 2 to a predetermined stop.
13. Close ball valve 2 and slowly release pressure from connector pipe 5 and the annulus of reach pipe 7, by opening the bleed-off valve contained on pressure regulating assembly 4.
14. Release female camlock 3 and remove the embodiment of the present invention from valve 2 and associated male cam lock.

As will be appreciated by those skilled in the art, the present invention teaches an apparatus which is configured to be inserted into a pressurized vessel through an existing valve, when the valve is opened, without disturbing the pressurized environment in the vessel. But, of course, such a valve functions as a barrier from permitting pressure to be released to the ambient. According to the present invention, the combination of connector pipe, reach pipe and control pipe configured as described herein provide, in essence, a telescopic pressure chamber which effectively functions as an extension of the pressurized vessel. Before connector pipe 5 is sealably attached to open valve 2, standard quick connect/disconnect cam locks are preferably positioned as hereinbefore described. In particular, a male cam lock, functioning as a counterpart to ball valve 2, is mated therewith. Female cam lock 3 is attached connector pipe 5 (see FIG. 2), akin to a conventional garden hose connection. Nonetheless, an embodiment of the present invention may be configured with any other suitable attachment devices which are consistent with the teachings and purposes described herein.

As should be clear to those skilled in the art, the seal provided by the present invention for performing in situ inspections of the interior surfaces of vessels under pressure is accomplished by three components which completely seal off connector pipe 5. First, the present invention provides a quick connect/disconnect means to open bore valve 2, as has been hereinbefore described. Second, the present invention provides a sealed annulus between connector pipe 5 and reach pipe 7. Third, a sealed annulus between reach pipe 7 and tilt control pipe 11 is provided. Reciprocating seals, functioning as a hydraulic ram, permit reach pipe 7 to be introduced into the pressurized environment contained within connection pipe 5 and then the same environment contained with the vessel, per se. If necessary, to maintain the position of reach pipe 7 under high pressure conditions (greater than about 30 psi), counterweights may be added to plurality of eyes 80 affixed to rotatable securing ring 8.

As should be clear to those skilled in the art, FIG. 2 depicts the relationship between the connector pipe, reach pipe, control pipe and flex pipe taught by the present invention, after an embodiment thereof has been placed within a vessel's pressurized environment and FIG. 3 depicts this corresponding relationship after the embodiment has been sufficiently introduced into the vessel to cause tilting of its camera housing. It should be clear that connector pipe 5 has been completely sealed off to echo the same pressure conditions existing within the vessel being inspected. The methodology taught by the present invention prevents contaminants from entering the pressurized vessel immediately before (during inspection set-up), during and immediately after (during inspection tear-down) inspection. In the instance of using an embodiment of the present invention to inspect a railway tank car, a typical reach pipe is 70" long which enables the camera housing to reach within 2 feet of the bottom. For a tankcar of 8 foot diameter, a typical connector pipe is 1 foot to 16 inches long, with an 2½ inch inside diameter. Of course, the reach and the like of the present invention is easily monitored by a worker familiar with the operation thereof. As generally portrayed in FIGS. 2 and 3, a connector pipe configured according to the present invention experiences a displacement of 60–70%.

It should be noted that if a pressurized vessel contains or is believed to contain hazardous materials, a suitable hose or pipe means may be preferably threadably interconnected with a bleed-off valve included on pressure regulating assembly 4, to safely collect any such materials.

The present invention also provides a manipulation ability wherein rotation of its camera housing may be accomplished through 360° and firing thereof may be accomplished through about 130°. Tilting is performed by the bending action of flex pipe or hose 18 which is fixedly attached to reach pipe 11 on one end and camera housing 16 on the other opposite end, and by the concomitant effect of a strap means 15 obliquely attached to this camera housing and slide ring 13. Once the travel of reach pipe 7 through open valve 2 has been completed, slide ring 13 being seated upon retaining means 14, applying further pressure upon insertion means or handle 12 causes fie-back strap 15 to become under tension and flex pipe 18 to bend, thereby causing camera housing 16 to tilt, which, in turn, causes camera port 17 to be exposed to different interior surfaces of the vessel being inspected and videotaped. As should be evident to those skilled in the art, Teflon coated materials may be advantageously used to reduce galling and the like on stainless steel surfaces and to simultaneously promote sliding. Typical applications of such Teflon coating include reach pipe 7 and control 11.

To provide acceptable viewing performance, front cap or port 17 of camera housing 16 preferably contains three lenses. Port window 17, is preferably constructed from optical grade sapphire to provide a tough surface to withstand impact with interior surfaces of a vessel and the like. Two Plano convex lenses, configured akin to conventional flash light bulbs, are preferably included to provide broad coverage by rendering narrow light beams into wide angles of protrusion 19. It should be noted that while an umbilical cable 23 as depicted in FIG. 1 may extend as long as 1,000 ft. from the situs of in situ inspection as herein described, a 5,000 ft. umbilical cable could be provided, if necessary, as long as a line driver is used.

The materials from which embodiments of the present invention may be constructed will be described, but only for illustrative, not limitation, purposes. Other suitable materials known to those skilled in the art may, of course, be used where advantageous either on an availability, cost or performance basis. Quick disconnect male and female cam locks are preferably constructed from stainless steel. Reach pipe 7 is preferably constructed from 304 stainless robing with 0.060 thickness and Teflon coating threaded on both ends at 28 threads per inch for 1" in length on outside diameter. Connector pipe 5 is preferably constructed from 2" pipe schedule 40 stainless steel. Pressure regulating assembly 4 is preferably constructed from stainless steel with associated pressure gauge having a 100 psi rating oil filled ¼ inch, ¼ turn valve. Reciprocating seals 6 and 10 should preferably be chemical resistant nitrile O-rings, e.g., manufactured by Parker, with Parbaks on both sides.

As hereinbefore described, if counterbalancing weights are needed for stable operation of the present invention, 5 and 10 pound lead weights configured with nylon web and swivel trigger snaps may be used to be attached to plurality of eyes 80 contained on rotating locking ring 8. To assure smooth operation of the present invention under typical pressure conditions thrust beatings 9 preferably comprise Thorington type closed design to enable rotation in a horizontal plane to effectively shock and the like. Tilt control pipe 11 should preferably have 0.048 thickness, with compression fitting to mate with flex pipe 18 on one end and handle 12 with rubber grips on the other opposite end. According to the teachings of the present invention, tilt control pipe 11 is mated via non-swivel connections on each of its ends to enable the full range of manipulation afforded. Tilt control slide ring 13 should preferably be configured with stainless steel having an outside diameter 0.020 less than the inside diameter of reach pipe 7 and 0.020 more than the outside diameter of tilt control pipe 11. Reach pipe retainer 14 is preferably stainless steel 28 TPI inside diameter and 0.250 larger than outside diameter of reach pipe 7. Tilt control tieback strap 15 is preferably constructed from stainless steel 0.010 thick 5/16" wide and of suitable length relative to flex pipe 18 and camera housing 16. For example, in the preferred embodiment, strap 15 is pre-measured to a length of 6¼" to achieve a tilt of 130°. As should be evident to those skilled in the art, other embodiments may be constructed with varying length straps to achieve different tilt angles. For example, a shorter strap results in a shorter control pipe stroke, which produces a larger angle of tilt. In accordance with the preferred embodiment, there are provided spot-welded loops disposed at each end of strap 15 for connection with slide ring 13 and camera housing 16, using suitably sized roll pins.

Pressure proof camera housing 16 is preferably constructed with wall 0.125 thick, 316 stainless steel, having rear cap with nitrile O-ring seal and compression fitting on outer end to mate with flex pipe 18. Similarly, front cap 17 has nitrile O-ring seal, 1-lens window 3 mm thick sapphire, which is, of course, optical grade for camera lens view port; two Plano-convex lenses for two fiber optic light strands are placed left and right of field of view 19. As will be appreciated by those skilled in the art, a sapphire optical glass lens affords an excellent combination of toughness and heat resistance. Flex pipe 18 preferably comprises stainless steel reinforced Teflon vacuum type hose with non-swivel assembly on both ends. As has been hereinbefore described, flex pipe 18 mates with control pipe 11 and rear cap (opposite of front cap 17) of camera housing 16; through tilt control pipe 11 there is thus provided a means to access camera housing 16 from outside of vessel 1, to remove any contained oxygen by injecting pressurized 100% gaseous nitrogen.

CCTV color module 22 is preferably a ½" CCD chip with 480 lines, horizontal resolution 0.2 lux min. illuminator Y.C. output, with a 12 VDC power input; having a 6 mm, f-1.2 aperture lens with automatic iris. A typical camera module is Sony "hyper head" unit. It will be appreciated that a remote head camera can also be used but the length of remote operation is limited to 30 meters. Field of view angle 19 of camera housing front cap 17 is 60° diagonal focus adjustable 6" to 20'. Optical grade glass fiber strand 20 has 0.187 diameter. with stainless steel ferrules and two 0.140 distal end legs. Light source 21, disposed at opposite end of optic fiber 20 proximal to camera housing 16, comprises 150 watt at 24 volt D.C. with variable transformer. Power supply for light source 25, typically located proximal to light source 21, enables adjustment of light output to bulb. Dual coax cables 23 preferably comprise 0.75 ohms Belden type cable. Power supply 27 is disposed proximal to light source 21 and preferably comprises a balanced 12 Volt D.C. power supply. Camera housings embodying the present invention have been found to be useful at pressures as high as 150 psi, and are rated to pressures of 75 psi.

As is appreciated by those skilled in the art, it is advantageous to use optic fibers to communicate illumination from a light source disposed outside a pressurized vessel to camera lens means disposed at front cap of the camera housing taught herein, because such fibers produce cool light. This, of course, is particularly important for such vessels as railway tankcars which are often subject to intense internal heat because of prolonged exposure to the sun. Indeed, if the internal heat of such a tankcar exceeds about 120° F., the camera contained within its housing may be operationally impaired.

As is also appreciated by those skilled in the art, it is advantageous to adjust lighting with dark interior surfaces to avoid reflection of light therein. This, of course, degrades the images captured during inspection.

Embodiments of the present invention have been tested in the field with remarkable results. For example, the Miles Inc. Materials Handling Department in Baytown, Texas has used embodiments of the present invention to further its interest promoting a hazard-free, environmentally-safe and reliable vehicle for inspecting railway cars. The conventional method for inspecting pressurized vessels may be broken down into the following stepwise tasks:

| Step | Task | Est. Time | Workers |
|---|---|---|---|
| 1 | Open vent valve and bleed pressure from tankcar | 60 min. | 1 |
| 2 | Wear protective clothing, gloves and air mask. | 15 min | 3 |
| 3 | Loosen dome bolts and open manway | 30 min | 3 |
| 4 | Inspect entire surface of tankcar interior | 15 min | 3 |
| 5 | Close dome and tighten dome bolts; change gasket if necessary | 30 min | 3 |
| 6 | Evacuate air | N/A | |
| 7 | Repressurize tankcar with nitrogen | 5 min | 1 |
| 8 | Inspect exterior of tankcar | 5 min | 1 |
| | TOTAL TIME | 160 min | |

Thus, a typical tankcar inspection performed heretofore consumes about 160 minutes and requires as many as three workers, corresponding to about 340 worker-minutes or 5.67 worker-hours per tankcar. The following shows the dramatic improvement achieved due to embodiments of the present invention:

| STEP | TASK | TIME |
|---|---|---|
| 1 | Install apparatus into tankcar | 5 min |
| 2 | Inspect entire inner surface of tankcar | 3 min |
| 3 | Remove apparatus from tankcar | 5 min |
| 4 | Inspect exterior of tankcar | 5 min |
| | TOTAL TIME | 18 min |

It is clear that there was an significant reduction of time consumed, from about 160 minutes to less than 20 minutes. To further dramatize these results, however, it should be noted that only one worker was needed throughout. Obviously, in addition to the severalfold savings in worker-time there was a concomitant reduction in the cycle time for inspections. It should be apparent that a consequence of such improved inspection cycle times is that tankcars and the like are more readily available for use.

As another benefit, the present invention generally may eliminate the need for special clothing and even air masks during the pressurized vessel inspection process, perhaps except under exigent circumstances. Since the results of this inspection may be conveniently recorded using the present invention, a record of the appearance of pressurized vessel interiors may be documented historically. Of course, since tankcars and other pressurized vessels are not opened during inspections, contamination therefrom is virtually eliminated.

But, as is well known by those skilled in the art, not only is this type of inspection time-consuming and labor-intensive, but also is a hazardous job because of the possible presence of industrial wastes, chemical byproducts and contaminants. In addition, from an operational standpoint, there is considerable downtime of tankcars and the like because of scheduling inspections thereof.

Other variations and modifications will, of course, become apparent from a consideration of the structures and techniques hereinbefore described and depicted. Accordingly, it should be clearly understood that the present invention is not intended to be limited by the particular features and structures hereinbefore described and depicted in the accompanying drawings, but that the concept of the present invention is to measured by the scope of the appended claims herein.

What is claimed is:

1. An apparatus for in situ inspection of all of the interior surfaces of a vessel having pressurized contents and an exterior valve means disposed on an exterior surface of said vessel for regulating said pressure therein, said apparatus comprising:

a rigid connector pipe means releasably and sealably attached while maintaining said pressure in said vessel by means of a dry seal at one end to said exterior valve means and configured at its other opposite end to axially and sealably by means of a dry seal receive a concentric rigid reach pipe means;

said rigid reach pipe means configured at one end to be rotatably and slidably received by said rigid connector pipe means and to be journalled therein, and further configured at its other opposite end to slidably and sealably by means of a dry seal receive a rigid tilt control pipe means;

said rigid flit control pipe means disposed axially and sealably by means of a dry seal within said rigid reach pipe means and configured to be journalled therein, and having a camera housing assembly manipulatively attached at an end thereof and having at its opposite end an insertion means for telescopically inserting said rigid tilt control pipe means within said rigid reach pipe means into said pressurized vessel, and, in turn, for tilting said camera housing assembly relative to said rigid tilt control pipe means; and a conduit means axially contained within said rigid flit control pipe means enclosing an umbilical cable means for communicating video signals between said camera housing assembly and external viewing and recording means;

said conduit means also enclosing a fiber optic cable means for communicating light from an external light source to said camera housing assembly for illuminating said interior surfaces of said pressurized vessel.

2. The apparatus recited in claim 1, wherein said insertion means comprises handle means.

3. The apparatus recited in claim 1, wherein said camera housing assembly comprises a flexible pipe means fixedly attached to said tilt control pipe means on one end and fixedly attached to a camera housing means at its other opposite end.

4. The apparatus recited in claim 3, wherein said camera housing means comprises a camera means and corresponding lens means.

5. The apparatus recited in claim 3, wherein said camera assembly means comprises a strap means fixedly attached at one end to a slide ring means configured to be slidably disposed circumferentially of said rigid tilt control pipe means with said strap means fixedly attached to said camera housing means at its other opposite end, for causing said flexible pipe means to bend as said tilt control pipe means is inserted into said reach pipe means, and, in turn, for causing said camera housing means to tilt after said slide ring means is slidably received by a retainer means disposed at said end of said reach pipe means which receives said tilt control pipe means.

6. The apparatus recited in claim 1, wherein said connector pipe comprises a pressure adjustment means, for equalizing pressure within said vessel and within said connector pipe means.

7. An apparatus for in situ inspection of all of the interior surfaces of a vessel having pressurized contents and an exterior valve means disposed on an exterior surface of said vessel for regulating said pressure therein, said apparatus comprising:

a rigid connector pipe means releasably and sealably attached while maintaining said pressure in said vessel by means of a dry seal at one end to said exterior valve means and configured at its other opposite end to axially and sealably by means of a dry seal receive a concentric rigid reach pipe means;

said rigid reach pipe means configured at one end to be rotatably and slidably received by said rigid connector pipe means and to be journalled therein, and further configured at its other opposite end to slidably and sealably by means of a dry seal receive a rigid tilt control pipe means;

said rigid tilt control pipe means disposed axially and sealably by means of a dry seal within said reach pipe means and configured to be journalled therein, and having a camera housing assembly manipulatively attached at an end thereof and having at its opposite end an insertion means for telescopically inserting said rigid tilt control pipe means within said rigid reach pipe means into said pressurized vessel, and, in turn, for tilting said camera housing assembly relative to said rigid tilt control pipe means;

said camera housing assembly comprising a flexible pipe means fixedly attached to said rigid tilt control pipe means on one end and fixedly attached to a camera housing means at its other opposite end; and a conduit means axially contained within said rigid tilt control pipe means enclosing an umbilical cable means for communicating video signals between said camera housing assembly and external viewing and recording means;

said conduit means also enclosing a fiber optic cable means for communicating light from an external light source to said camera housing assembly for illuminating said interior surfaces of said pressurized vessel.

8. The apparatus recited in claim 7, wherein said insertion means comprises handle means.

9. The apparatus recited in claim 7, wherein said camera housing means comprises a camera means and corresponding lens means.

10. The apparatus recited in claim 7, wherein said camera assembly means comprises a strap means fixedly attached at one end to a slide ring means configured to be slidably disposed circumferentially of said rigid tilt control pipe means with said strap means fixedly attached to said camera housing means at its other opposite end, for causing said flexible pipe means to bend as said tilt control pipe means is inserted into said reach pipe means, and, in turn, for causing said camera housing means to tilt after said slide ring means is slidably received by a retainer means disposed at said end of said reach nine means which receives said tilt control pipe means.

11. The apparatus recited in claim 7, wherein said connector pipe comprises a pressure adjustment means, for equalizing pressure within said vessel and within said connector pipe means.

12. An apparatus for in situ inspection of all of the interior surfaces of a vessel having pressurized contents and an exterior valve means disposed on an exterior surface of said vessel for regulating said pressure therein, said apparatus comprising:

a rigid connector pipe means releasably and sealably attached while maintaining said pressure in said vessel by means of a dry seal at one end to said exterior valve means and configured at its other opposite end to axially and sealably by means of a dry seal receive a rigid concentric reach pipe means;

said rigid reach pipe means configured at one end to be rotatably and slidably received by said connector pipe means and to be journalled therein, and further configured at its other opposite end to slidably and sealably by means of a dry seal receive a rigid tilt control pipe means;

said rigid tilt control pipe means disposed axially and sealably by means of a dry seal within said rigid reach pipe means and configured to be journalled therein, and having a camera housing assembly manipulatively attached at an end thereof and having at its opposite end an insertion means for telescopically inserting said rigid tilt control pipe means within said rigid reach pipe means into said pressurized vessel, and, in turn, for tilting said camera housing assembly relative to said rigid tilt control means;

said camera housing assembly comprising a flexible pipe means fixedly attached to said rigid tilt control pipe means on one end and fixedly attached to a camera housing means at its other opposite end;

said camera housing assembly further comprising a strap means fixedly attached at one end to a slide ring means configured to be slidably disposed circumferentially of said rigid tilt control pipe means with said strap means fixedly attached to said camera housing means at its other opposite end, for causing said flexible pipe means to bend as said rigid tilt control pipe is inserted into said rigid reach pipe means, and, in ram, for causing said camera housing means to tilt after said slide ring means is slidably received by a retainer means disposed at said end of said reach pipe means which receives said tilt control pipe means;

said reach pipe means including a retaining ring means fixedly attached thereto at said end thereof proximal to said flexible pipe means and configured to receive said slide ting means, for limiting said bending of said flexible pipe means; and a conduit means axially contained within said rigid tilt control pipe means enclosing an umbilical cable means for communicating video signals between said camera housing assembly and external viewing and recording means;

said conduit means also enclosing a fiber optic cable means for communicating light from an external light source to said camera housing assembly for illuminating said interior surfaces of said pressurized vessel.

13. The apparatus recited in claim 12, wherein said insertion means comprises handle means.

14. The apparatus recited in claim 12, wherein said camera housing means comprises a camera means and corresponding lens means.

15. The apparatus recited in claim 12, wherein said connector pipe comprises a pressure adjustment means, for equalizing pressure within said vessel and within said connector pipe means.

16. The apparatus recited in claim 5, wherein said reach pipe memos includes a retaining ring means fixedly attached thereto at said end thereof proximal to said flexible pipe means and configured to receive said slide ring means, for limiting said bending of said flexible pipe means.

17. The apparatus recited in claim 7, wherein said reach pipe means includes a retaining ring means fixedly attached thereto at said end thereof proximal to said flexible pipe means and configured to receive said slide ting means, for limiting said bending of said flexible pipe means.

* * * * *